United States Patent [19]
Amor, Jr. et al.

[11] 3,986,697
[45] Oct. 19, 1976

[54] TELESCOPIC COLUMN FOR X-RAY APPARATUS

[75] Inventors: William H. Amor, Jr., Auburn Township; Robert J. Steffek, Wickliffe, both of Ohio

[73] Assignee: Picker Corporation, Cleveland, Ohio

[22] Filed: Nov. 21, 1973

[21] Appl. No.: 418,128

[52] U.S. Cl. .................................. 248/333; 403/52
[51] Int. Cl.² ...................................... A61B 19/00
[58] Field of Search ................... 248/161, 327, 333; 108/144; 250/523; 403/52

[56] References Cited
UNITED STATES PATENTS

| | | | |
|---|---|---|---|
| 2,400,348 | 5/1946 | Greene | 151/41.73 X |
| 2,823,960 | 2/1958 | Blazek et al. | 403/52 X |
| 2,835,520 | 5/1958 | Schiring et al. | 248/333 UX |
| 2,854,078 | 9/1958 | Conner | 108/144 UX |
| 2,909,665 | 10/1959 | Guentner et al. | 250/523 |
| 3,285,207 | 11/1966 | Vom Hagen | 108/144 |
| 3,481,286 | 12/1969 | La Mar et al. | 108/144 UX |
| 3,521,341 | 7/1970 | Hornlein et al. | 248/161 X |
| 3,776,500 | 12/1973 | Foderaro | 248/333 |

FOREIGN PATENTS OR APPLICATIONS

| | | | |
|---|---|---|---|
| 286,709 | 2/1965 | Netherlands | 108/144 |
| 1,054,667 | 1/1967 | United Kingdom | 248/333 |

*Primary Examiner*—William H. Schultz
*Attorney, Agent, or Firm*—Watts, Hoffmann, Fisher & Heinke Co.

[57] ABSTRACT

An X-ray apparatus includes a telescopic column support with concentrically positioned tubular sections nested one within another. Each of the sections except its innermost section has three guide bars triangularly spaced on the inner surface. Each section except the outermost section has rollers on its outer surface co-operating with the adjacent guide bars of the surrounding section. The guide bars cooperate with the rollers in a generally circumferential direction rather than radially of the tubular members. Mounting plugs held in apertures of the telescopic sections by an interference fit mount the guide bars and rollers. The plugs are initially insertable into the apertures with a clearance fit, when an appropriate temperature differential is established between the plugs and sections. A pulley wheel outside a fixed column section and carried by the first movable section supports a loop of control and power cables to take up and release the cables relative to a fixed location on a subsequent section, and at a rate equal to the change in length of the column, thereby avoiding slack in the cable during extension and retraction of the column.

22 Claims, 8 Drawing Figures

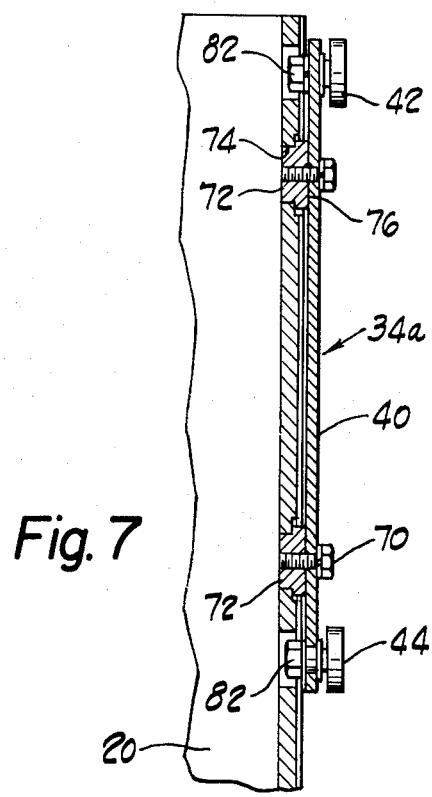
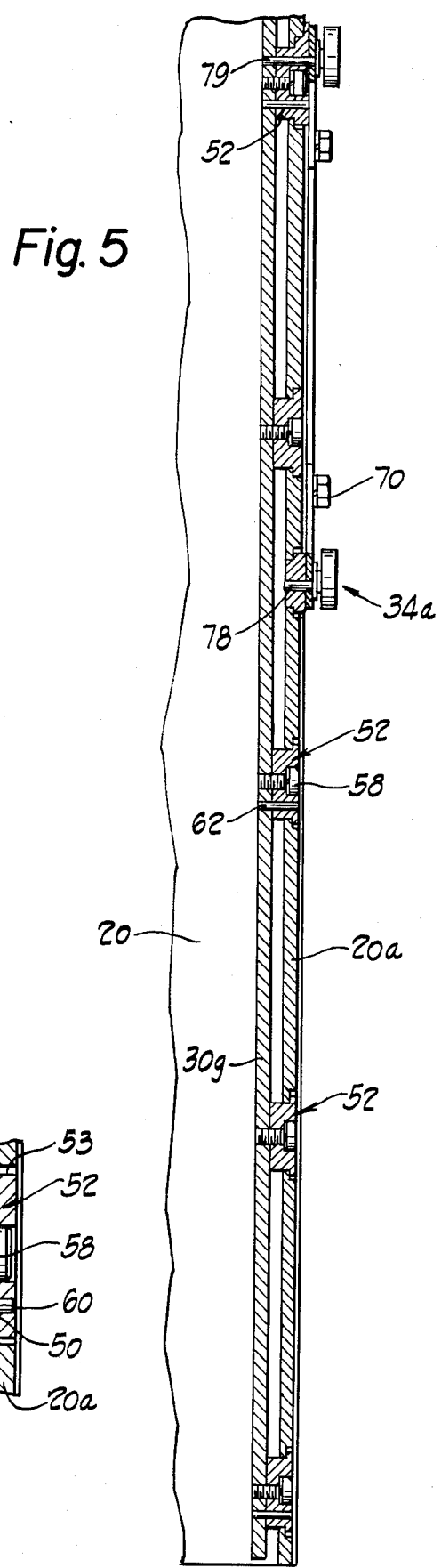
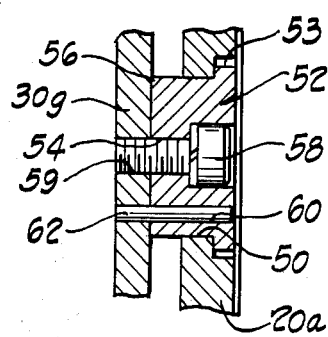
Fig. 5
Fig. 7
Fig. 6

TELESCOPIC COLUMN FOR X-RAY APPARATUS

CROSS-REFERENCE TO RELATED PATENT AND APPLICATIONS

Application Ser. No. 418,051 of William H. Amor and Anthony T. DiFranco, entitled Fail-Safe Telescopic Support System for X-Ray Apparatus, filed Nov. 21, 1973, hereinafter the "Support System Patent."

Application Ser. No. 418,057 of William H. Amor and Robert E. Stancliff, entitled Mount for Ceiling Supported X-Ray Tubes, filed Nov. 21, 1973, hereinafter the "Mount Patent."

The disclosures of the referenced applications are incorporated herein by reference.

U.S. Pat. No. 3,776,500 issued Dec. 4, 1973, to Anthony J. Foderaro, entitled X-Ray Apparatus Having a Telescopic Columnar Support.

BACKGROUND OF THE INVENTION

1. Field of the Invention

This invention relates to X-ray apparatus having a telescopic column and to a method of constructing such a column.

2. Prior Art

X-ray apparatus provided with telescoping supports of various types are well known. While telescoping supports are desirable due to their inherent strength and compact construction, most known telescopic supports present a number of problems when used in conjunction with X-ray equipment.

The forces which X-ray apparatus imposes on telescopic supports are both large in magnitude and variable in direction depending upon the positioning of the apparatus. The X-ray tube housing, support, and associated counterweight mechanisms are inherently heavy, and impose lateral forces on the telescoping sections which vary in accordance with the position of the apparatus. The X-ray tube power cables which connect with the tube housing are also heavy, bulky, and serve to impose forces on the column that vary with position.

One problem with typical telescopic columns is that the guide structure for telescoped sections is not constructed to minimize accumulated play in a radial direction of the telescopic sections, and therefore they are less rigid than desired, especially when fully extended. A further problem is that it is difficult and expensive to construct telescoping parts with accurate fits so that small tolerances can assure maximum rigidity, yet provide smooth operation. Typically, the telescopic construction does not lend itself to readily fabricating columns of different lengths, without changing the tooling, setup fixtures, etc. This is especially true where the telescopic sections include specialized end formations that prevent their being simply cut off to provide shorter sections. Hence, with such sections, the length of a column to be constructed is limited by the range of lengths and diameters of sections available.

SUMMARY OF THE INVENTION

The present invention overcomes the foregoing and other drawbacks of prior art X-ray apparatus supports. In particular, it provides an X-ray apparatus with an improved telescopic column formed of extruded sections with guide structure attached accurately and conveniently, which is economical to fabricate, and which results in an extremely rigid interconnection between the sections, reducing accumulated error radially of the axis of the column during column extension.

In accordance with the present invention, a telescopic column support is provided comprising concentrically positioned tubular sections nested one within another. All of the sections except the outermost sections serve as "nested" sections while all of the sections except the innermost section serve as "nesting" sections. The nesting sections each have a plurality of guide bars extending longitudinally of their interior surfaces each section carries a plurality of guide rollers or guide bearings on its exterior. The rollers cooperate with the guide bars to keep the sections aligned during extension of the column.

The guide bars carried by the nesting sections provide two guide surfaces in a plane peripherally oriented relative to the sections; i.e., the planes of the guide bars on which the guiding surfaces are located do not pass through the central axis of the column section. Preferably, three guide bars are provided in planes that are oriented in a triangular relationship, most advantageously in an equilateral triangular relationship. Rolls carried by the nested sections straddle the guide bars and ride along the guide surfaces. Any accumulative error due to play between the rollers and the guide bars is in a peripheral or circumferential direction and is substantially minimized in a radial direction. This assures the accurate positioning of the axis of the column even when the column is fully extended. It further resists twisting movements extremely effectively.

This invention provides an advantageous construction for securing the guide bars and the rollers accurately to the extruded sections of the column support, notwithstanding any lack of straightness of the supporting walls of the sections. To this end, apertures are formed along the longitudinal extent of each extruded section, along which the guide bars are located. Apertures are further provided adjacent the locations of the rollers that cooperate with the guide bars of adjacent sections. Plugs are inserted into the apertures to provide accurate locating surfaces for the guide bars and support plates of the rollers. The guide bars are held in proper relationship to the supporting section, against a surface of each plug and extends beyond the surface of the section, by locating pins and threaded fasteners. The distance by which individual plugs extend from the surface of the section in which they are mounted are selected to assure that the guide bars are straight even if the tubular extrusion forming the carrier for the bars is warped. In the same manner, the mounting plates that carry the rollers are secured to the sections, but on opposite sides from the guide bars, for cooperating with the bars of an adjacent section.

In the preferred embodiment, the plugs are secured in the apertures through a friction fit. Insertion of the plugs into the apertures is facilitated by establishing a temperature differential that provides a clearance between the aperture and the plug during assembly. By this arrangement, the extruded sections may be formed from relatively soft and easily machined materials. In addition, the sections and the guide bars may be cut to any desired length, thereby providing a telescopic column which is simple and inexpensive to manufacture in a wide range of lengths. The manner of mounting the guide bars and rollers provides accurate alignment with a minimum of assembly time.

Another feature of this invention is the provision of a cable-carrying pulley secured to a movable section of the column. The pulley takes up and pays out cable as the column length is changed to keep a central portion of the cable substantially straight and out of the way of both the operator and equipment.

Accordingly, it is a principal object of the present invention to provide and X-ray apparatus with a novel and improved telescopic column support.

The above and other objects, features and advantages of this invention will be better understood by reference to the following description, when considered in conjunction with the accompanying drawings.

BRIEF DESCRIPTION OF THE DRAWINGS

FIG. 5 is a longitudinal sectional view as seen from the plane indicated by the line 5—5 of FIG. 3;

FIG. 6 is a partial enlarged view of a plug as shown in FIG. 5;

FIG. 7 is a longitudinal sectional view as seen from the plane indicated by the line 7—7 of FIG. 3; and, FIG. 8 is a partial perspective view of the column of FIG. 1, viewed from the opposite side, with parts removed, illustrating the manner in which the control and power cable is carried along a portion of the column.

DESCRIPTION OF THE PREFERRED EMBODIMENT

Figure 1:
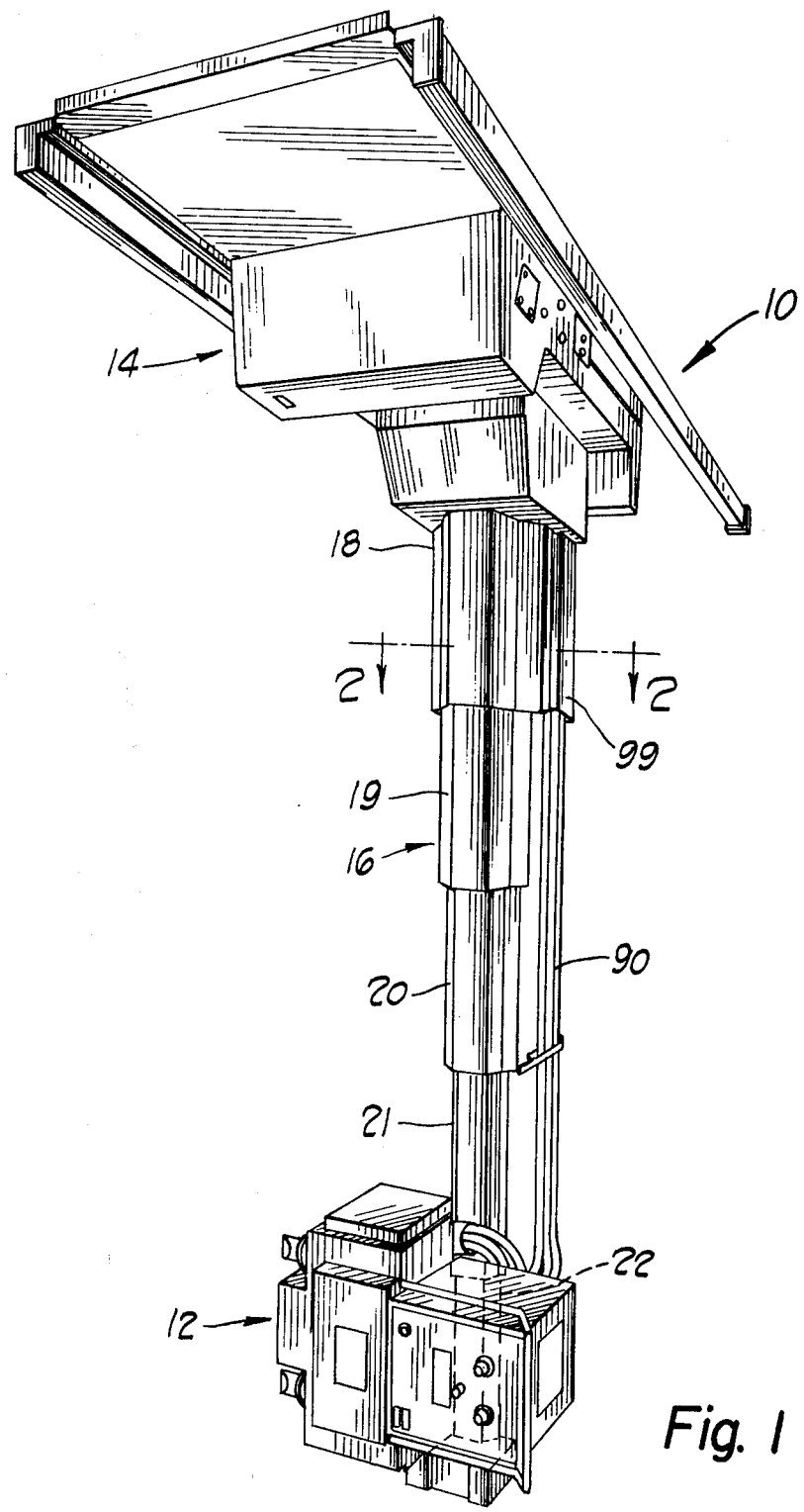
FIG. 1 is a perspective view of the X-ray apparatus of the present invention illustrating the telescopic column extended.

Referring to FIG. 1, an X-ray apparatus is shown generally at 10. The X-ray apparatus 10 includes an X-ray tube housing assembly 12, which is supported from an overhead support assembly 14 by a telescopic column 16. The column 16 is comprised of a plurality of concentric tubular column sections 18, 19, 20, 21 and 22 in nested and nesting relationship, and movable from a retracted position in which the sections are each substantially completely contained within the section 18, to an extended position as shown in FIG. 1.

Figure 2:
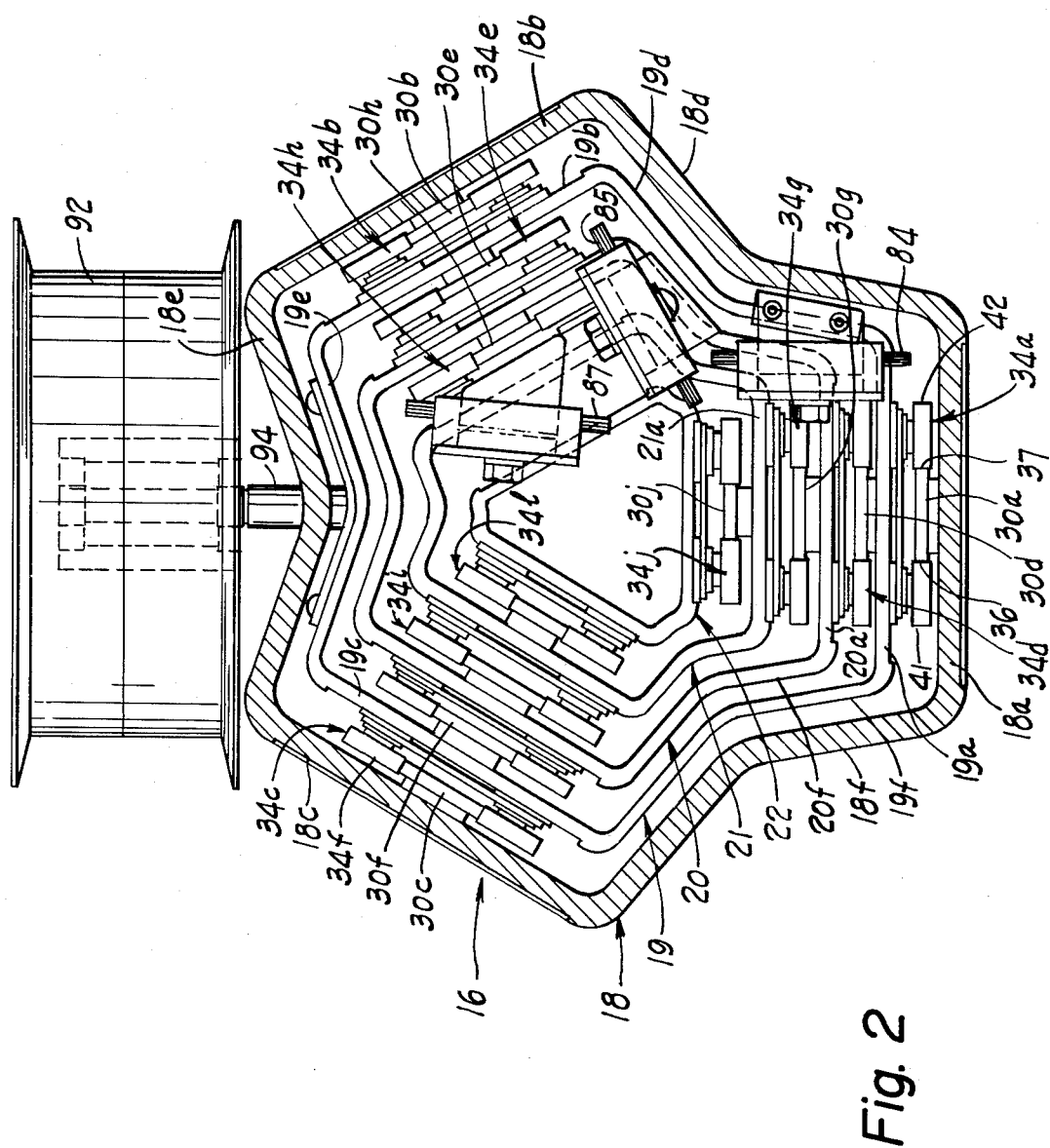
FIG. 2 is a sectional view of the column of FIG. 1, as seen from the plane indicated by the line 2—2 of FIG. 1.

Each column section 18–22 had a cross-sectional shape as shown in FIG. 2. More particularly, each includes three flat surfaces indicated by the reference numeral of the section along with a designation $a, b, c$. Each flat surface is spaced by three concave surfaces designated by the reference numeral of the section plus the designation $d, e, f$. The flat surfaces $a, b, c$ of each section 18–22 serve to support guide plates or rollers, or both, for supporting the sections in a concentric relationship, for relative longitudinal movement.

In the preferred embodiment, the flat sides that form any one of the sections 18–22 are equal in width and length, and are oriented at angles of 60' one to the other, equally spaced from each other, and thus lie in planes that define in cross-section an equilateral triangle. The widths of the sides of the different sections 18–22 are different, to facilitate nesting of the sections and to provide a clearance between the telescoped sections for guide plates 30 and roller assemblies 34, which cooperate with each other to retain the sections in concentric relationship and to facilitate relative telescopic movement.

Three guide plates are carried by each section 18–21, which are nesting sections. Thus, guide plates 30$a, b, c$ are supported on the inside surfaces of flat sides 18$a, b, c$; guide plates 30$d, e, f$, are supported on inside surfaces of flat sides 19$a, b, c$; guide plates 30$g, h, i$ are supported on inside surfaces of flat sides 20$a, b, c$; and guide plates 30$j, k, l$ are supported on inside surfaces of flat sides 21$a, b, c$. The guide plates 30 are located centrally of the widths of each side of the supporting section and extend the full length of the section. Thus, the guide plates also lie in planes at 60° with respect to the others and are equally spaced one from the other. Longitudinal side surfaces 36, 37 of each guide plate serve as roller guides for the next adjacent nested section.

Three roller assemblies are carried by each section 19–22, which are nested sections of the telescoped column. Thus, roller assemblies 34$a, b, c$ are support on the outside surface of each flat side 19$a, b, c$ of the section 19 and cooperate with the guide bars 30$a, b, c$ of the nesting section 18; roller assemblies 34$d, e, f$ are supported on the outside surface of flat sides 20$a, b, c$ and cooperate with guide bars 30$d, e, f$; roller assemblies 34$g, h, i$ are supported on the outside surface of flat sides 21$a, b, c$ and cooperate with guide bars 30$g, h, i$; and roller assemblies 34$j, k, l$ supported on the outside surface of flat sides 22$a, b, c$ cooperates with guide bars 30$j, k, l$.

Figure 4:
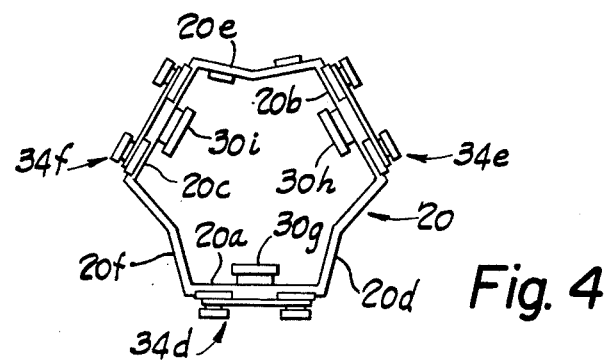
FIG. 4 is an end elevational view of the column section of FIG. 3.
Figure 3:
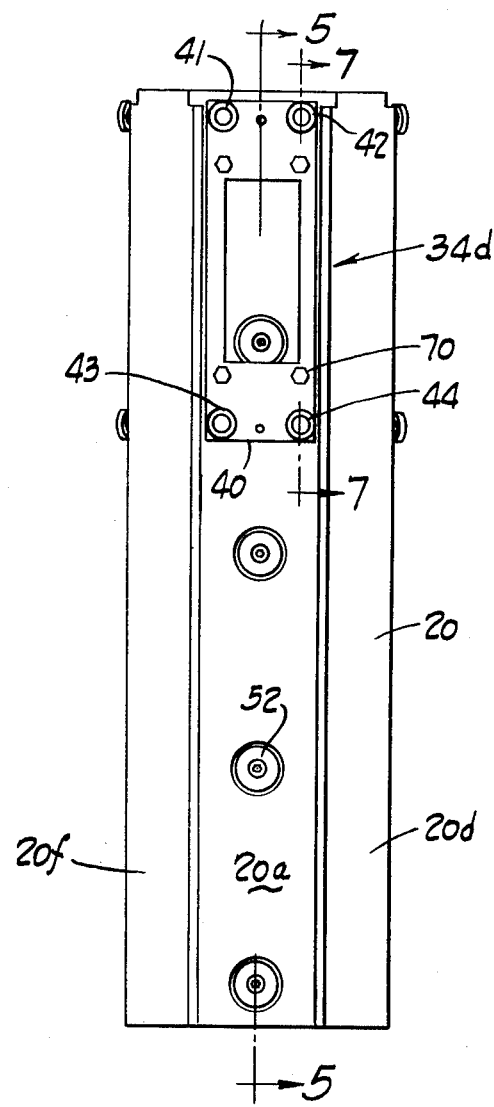
FIG. 3 is a front elevational view of one of the intermediate sections of the telescopic column shown in FIG. 2.

The roller assemblies 34, also shown in FIGS. 3 and 4 of the drawings, include a support plate 40 that is short relative to the length of each telescopic section, and each plate carries four rollers 41, 42, 43, 44 spaced transversely and longitudinally of the respective sections. The plate 40 is carried parallel to the guide bar with which the rollers cooperate, and the transverse spacing of the rollers is equal to the width of the guide bar so that the rollers run along the opposite surfaces 36, 37 of the guide bar. Each assembly 34 is located adjacent the upper end of the telescopic section to which it is secured and stays within the adjacent nesting section of the column, even when the column is fully extended.

The manner in which the guide bars 30 and roller supporting plates 40 are accurately located and secured to the sections of the column 10 is shown in FIGS. 5 to 7 with respect to the section 20 shown in FIG. 3. The manner in which the guide bars and roller supporting plates are secured to each section is substantially identical for all, except for the outer section 18 and the inner section 22, which do not support both guide bars and roller assemblies. In those cases, it will be apparent that one or the other of the securing arrangements will be omitted.

The flat side 20$a$ of the telescopic section 20 and the attachment of parts thereto will be described, it being understood that the construction and arrangement of each of the other flat sides 20$b$, 20$c$ is identical. Circular apertures 50 are provided in the flat side 20$a$ spaced along the length thereof and centered relative to the width. Each aperture is counterbored at the outer surface of the flat side 20$a$. The depth of the counterbore can be varied to control the location of one or the other of the end surfaces of the plugs to accommodate for any lack of straightness in the section wall.

Plugs 52, each with a cylindrical body and a flange 53 at one end, are located in the apertures 50. The plug body has a central aperture 54 that is counterbored in the end surface that is flanged. The size of the cylindrical body of the plugs is selected so that it will be received within an apertures 50 with an interference fit, when the section and the plug are at the same temperature. Also, the relative sizes of the plug body and aperture are selected so that, at a suitable temperature differential, the plug will fit within the aperture 50 with a slight clearance fit. Because both the tubular section and the plugs are metal, they will respond dimensionally to a substantial extent in response to a temperature change. Conveniently, the plugs are cooled in liquid nitrogen to reduce their dimensions relative to the size of the apertures 50 so they can be easily inserted into the apertures, but will return to a dimension that will cause them to be retained by friction when they reach the temperature of the section wall.

An end face 56 of the plugs 52 opposite the end that is flanged serves as a mounting surface for the guide bars. The guide bars are initially, during assembly, located accurately with respect to the section so as to extend longitudinally in accurate alignment with the central axis thereof. This is conveniently done with a suitable jig or fixture and, with the guide bar properly aligned, it is secured to the plugs against the end faces 56 with screws 58 having associated lock washers, the screws fitting through the central passage 54 and being threadedly received in apertures 59 of the bar. To avoid any possibility of the guide bar being forced out of proper alignment due to clearances between the plug apertures and the screws, holes 60 are drilled through selected plugs 52 and through the bar 30, and locating pins 62 are inserted to maintain the position of the guide bar 30 with respect to the section wall 20a. Alternatively, separate plugs similar to the plugs 50 but without the central aperture for the screws can be utilized for receiving the locating pins.

The plate 40 of the roller assembly 34 is secured to the outside surface of the flat side 20a by four machine screws 70 received in four plugs 72, two of which are shown in FIG. 7. The plugs 72 are received in counterbored apertures 74 in the flat side 20a, with a friction fit the same as the plugs 52 are secured in the apertures 50. Each of the plugs 72 has a flange 74 at one end, received in the counterbore of the aperture, but the depth or height of the flange is greater than the depth of the counterbore. This spaces a top mounting surface 76 of the plug from the outer surface of the flat side 20a, to provide a mounting surface for the plates 40, spacing them from the outer surface of the section wall. The depth of the counterbore can be controlled to assure that the surfaces 76 are accurately aligned in a common plane parallel to the plane of the guide bar with which it cooperates.

The plate 40 is accurately located by pins 78, 79 adjacent opposite ends, that extend through plugs. This is done by first locating the plate relative to the position of the guide bar 30 on the adjacent section with which it cooperates, e.g., section 19. The plate is then secured by the screws 70. Holes for the pins 78, 79 are then drilled in the plugs and the pins inserted to retain the plate 40 in the proper position. In the arrangement shown, a separate plug 80 is provided for the pin 78, and one of the plugs 52 used to secure the guide bar 30 receives the pin 79. Whether separate plugs or the plugs used to support the guide bar are used depends upon the convenience of the location relative to the mounting position of the plate 40. The rollers 41–44 are supported on the plate 40 by screws 82, spaced to straddle a guide bar and to run along the surfaces 36, 37.

Movement of the sections 19–22 of the telescopic column is controlled so that each nested section moves the same distance relative to its nesting section as the others. As a result, all sections extend progressively, each from the next simultaneously. The manner in which movement of the sections is effected and controlled is disclosed in the reference Support System Patent. Three pulleys 84–86 shown in FIG. 2 secured at the top of the movable intermediate sections 19–21 carry cables (not shown) that interconnect the sections.

Figure 8:
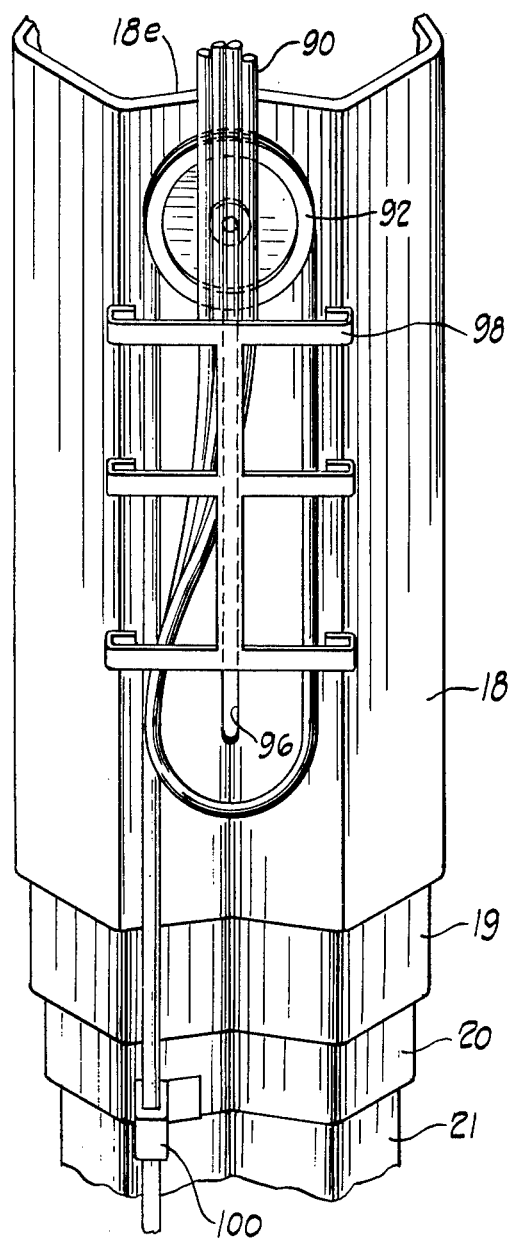

A bundle 90 of four power cables, as best shown in FIGS. 1 and 8, extends from the overhead support apparatus 14 to the housing assembly 12 at the end of the column 16. Pay out and take up of the cable bundle is conveniently, simply, and automatically controlled by a pulley wheel 92 carried by the first movable column section 19. The pulley wheel is supported on a pulley shaft 94 connected to the wall portion 19e of the section 19. The shaft extends through a longitudinal slot 96 (FIG. 8) in the wall portion 18e of the section 18, and the pulley wheel is supported outside the stationary section 18. With this arrangement, movement of the section 19 relative to the stationary section 18 moves the pulley wheel relative to the section 18.

The cable bundle 90 extends from the overhead support assembly 14 downward along the surface 18e of the section 18, to the outside of and across the pulley 92. The cable bundle is then looped back upward just above the lower end of the section 18, is carried around the top of the pulley 92 and then extends downward from the pulley along the section 18 and subsequent sections. The pulley loop is confined by a cage 98 secured to the section 18, and the cage and loop are then covered by a housing 99 (FIG. 1) with an opening at the bottom through which the cable extends. The cable bundle 90 is secured at the bottom edge of the third column section 20 in fixed relationship by a clamp 100.

With the above construction, when the sections 19–22 are extended, the pulley 92 will lower with the section 19, paying out a length of cable equal to twice the distance that the section 19 travels, because two sides of the cable loop are shortened by the distance the pulley moves toward the bottom of the loop. Because the cable is secured in fixed relationship to the third section 20, the fixed point of the cable at the bracket 100 will travel twice as far as the pulley 92, because it moves the combined distance of the sections 19 and 20. As a result, the movement of the bracket 100 precisely accommodates the pay out of the cable from the loop and pulley 92, resulting in a relatively taut or straight relationship of the cable bundle 90 along the column, between the bracket 100 and the housing 99. Upon retraction of the column sections, the pulley 92 moves upward relative to the sections 18, taking up the cable at a rate that accommodates the upward movement of the clamp 100, maintaining the cable in a straight path along the second and third sections of the column. The variation in cable length along the fourth and fifth sections is accommodated by a cable loop adjacent the X-ray housing assembly 12. This is acceptable because the change in length is occasioned only along two sections of the column and in fact is desirable to provide adequate cable for swinging the X-ray tube housing assembly about adjustment axes.

From the above description it will be apparent that a telescopic column support apparatus has been provided in which sections of the column are conveniently fabricated and accurately aligned, and which provides a convenient and automatic cable take up and pay out arrangement.

While the preferred embodiment of this invention has been described in detail, it will be understood that various modifications or alterations may be made therein without departing from the spirit and scope of the invention set forth in the sppended claims.

What is claimed is:

1. In an X-ray apparatus including a support and a mechanism for contributing to the production of an X-ray image, an improved telescopic column connecting the mechanism to the support comprising:
   a. a plurality of elongated tubular sections telescoped together for rectilinear extension and retraction;
   b. three spaced parallel guide bars carried by each of said sections except one, extending parallel to and being spaced from a central longitudinal axis of the sections;
   c. each of said bars having two parallel guide surface portions facing in opposite directions; and,
   d. a plurality of rotatable members carried by each of said sections except one at three different locations each adjacent one of three guide bars of an adjacent section, the plurality of rotatable members at each location being in contact with said oppositely facing guide surface portions of the adjacent guide bar and the individual rotatable members being in contact with only one of said oppositely facing guide surface portions, each said member having an axis of rotation oriented parallel to that of the other members at the same one of said three locations and at an angular, nonparallel and noncoincident, relationship to the orientation of the axes of rotation of said members at the other said locations.

2. The apparatus of claim 1 wherein said plurality of rotatable members on each of said sections includes at least three rotatable members cooperating with each of said guide bars.

3. The apparatus of claim 2 wherein each of said guide bars is carried near the inner surface of its carrying section, and said rotatable members and carried near the outer of their carrying sections.

4. The apparatus of claim 2 wherein:
   a. said rotating members are rollers;
   b. three plates are secured to each roller carrying section;
   c. said plates support said rollers;
   d. apertures are formed in each of said tubular sections adjacent said plates;
   e. plugs are carried in said apertures; and,
   f. mounting means secure said plates to said plugs.

5. The apparatus of claim 4 wherein said plates are located relative to said roller carrying sections by pins extending within aligned apertures formed in the plates and plugs, and said plugs spaced said plates from said roller carrying sections.

6. The apparatus of claim 3 wherein said plugs are secured to said roller carrying sections by an interference fit in said apertures.

7. The apparatus of claim 1 wherein said guide bars have a greater than thickness, and said surface portions extend across the thickness of said guide bars.

8. The apparatus of claim 1 additionally including apertures formed in said sections, plugs secured in said apertures, and wherein said guide bars are secured to said plugs.

9. The apparatus of claim 8 wherein each of said apertures has a counterbore, each of said plugs has a flange received in the counterbore and an end face against which its associated guide bar is secured, said face being spaced outwardly from the surface of its carrying section, and wherein locating pins position said guide bars relative to said sections.

10. The apparatus of claim 4 wherein each of said apertures has a counterbore, each of said plugs has a flange and an end face, said face being spaced from its carrying section, and wherein said plates are secured against said end faces of said plugs.

11. The apparatus of claim 1 wherein each section that carries both rotatable members and guide bars includes apertures with counterbores, plugs with flanges in said apertures and counterbores, one face of each plug being spaced from one of either the inside or outside surface of such section, a plate secured to said faces of plugs extending from one of said surfaces, and a guide bar secured to said faces of plugs extending from the other of said surfaces, and said rotatable members being carried by said plate.

12. The apparatus of claim 1 wherein said plugs are secured in said apertures by an interference fit.

13. The apparatus of claim 11 wherein the depth of each of said counterbores is selected to locate said faces of said plugs at substantially equal distances from said central axis.

14. In an X-ray apparatus including a support and a mechanism for contributing to the production of an X-ray image, an improved telescopic column connecting the mechanism to the support comprising:
   a. a plurality of elongated tubular members each having three flat longitudinally extending surfaces disposed in mutually intersecting planes of a substantially equilateral triangle and located substantially equidistantly from a common central longitudinal axis;
   b. flat roller guide bars carried on one side of said flat surfaces substantially parallel to and spaced therefrom and defining two parallel guide surfaces extending substantially perpendicular to the planes of their associated flat surfaces; and,
   c. three sets of guide rollers carried by each of said tubular members on the opposite side of said flat surfaces from said guide bars, the rollers of each of said sets being located adjacent both guide surfaces of the bars of a telescoped adjacent member, each roller being in contact with only one guide surface, the rollers of each set having axes of rotation oriented parallel to each other and at a 60°/120° angle relative to the orientation of the axes of rotation of the rollers of the other sets.

15. The apparatus of claim 14 wherein apertures are formed in said members opening through said flat surfaces, plugs are secured in said apertures and, said rollers and guide bars are secured to said plugs.

16. The apparatus of claim 15 wherein:
   a. each of said sets of rollers is carried on a support plate; and, b. pins extend through said plugs, said guide bars and said roller support plates to accurately locate said guide bars and said roller support plates relative to said members.

17. The apparatus of claim 16 wherein said plugs are secured in said apertures with an interference fit.

18. The apparatus of claim 1 wherein each of said sections has three spaced planar side walls and three curved walls interposed between and connecting said planar side walls and, said guide bars and said rotatable members are located between the planar side walls of adjacent ones of said sections.

19. The apparatus of claim 18 wherein the planar side walls of each section are oriented in planars which, if extended, would form substantially and equilateral triangle.

20. A telescopic column, comprising:
 a. a plurality of elongated tubular sections telescoped together for extension and retraction along a rectilinear path with all of said sections except the innermost one of said sections serving as a nesting section, and all but the outermost one of said sections being a nested section;
 b. each of the nesting sections having an inwardly oriented surface;
 c. each of the nested sections having an outwardly oriented surface paired and in space relationship with the closest inwardly oriented surface;
 d. one of the surfaces of each pair having three parallel guide bars extending longitudinally of and adjacently supported on its section;
 e. the other surface of each pair having three sets of rollers supported on its section;
 f. the guide bars on each pair being spaced from a central longitudinal axis of the sections, and each of said guide bars having two oppositely facing guide surfaces paralleling said central axis; and,
 g. each of said sets of rollers engaging a separate pair of said guide surfaces, any roller of each set engaging only one of said guide surfaces and having an axis of rotation oriented parallel to that of the other rollers of the set and at approximately a 60°/120° angle relative to the orientation of the axes of rotation of said rollers of the other sets.

21. The column of claim 20 wherein:
 a. each of said sections has three spaced planar side walls and three curved walls interposed between and connecting said planar side walls; and,
 b. said guide bars and said rollers are located between the planar side walls of adjacent ones of said sections.

22. The column of claim 21 wherein the planar side walls of each section are oriented in planes which, if extended, would form substantially an equilateral triangle.

* * * * *

UNITED STATES PATENT AND TRADEMARK OFFICE
CERTIFICATE OF CORRECTION

PATENT NO. : 3,986,697
DATED : October 19, 1976
INVENTOR(S) : William H. Amor, Jr., et al It is certified that error appears in the above-identified patent and that said Letters Patent are hereby corrected as shown below:

Col. 2, line 44, "and" should be -- that --

Col. 3, line 6, "and" should be -- an --

Col. 3, line 61, "60'" should be -- 60° --

Col. 4, line 20, "support" should be -- supported --

Col. 4, line 29, "cooperates" should be -- cooperate --

Col. 6, line 10, "reference" should be -- referenced --

Col. 6, line 59, "sections" should be -- section --

Claim 6, line 1, "3" should be -- 4 --

Claim 7, line 2, after "greater" insert -- width --

Claim 19, line 2, "planars" should be -- planes --

Claim 19, line 3, "and" should be -- an --

Claim 20, subparagraph c., line 2, "space" should be -- spaced --

Title Page, the drawing should be inverted.

Signed and Sealed this

First Day of February 1977

[SEAL]

Attest:

RUTH C. MASON
*Attesting Officer*

C. MARSHALL DANN
*Commissioner of Patents and Trademarks*